(12) United States Patent
Bern

(10) Patent No.: US 8,108,153 B2
(45) Date of Patent: Jan. 31, 2012

(54) METHOD, APPARATUS, AND PROGRAM PRODUCT FOR CREATING AN INDEX INTO A DATABASE OF COMPLEX MOLECULES

(75) Inventor: Marshall W. Bern, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1553 days.

(21) Appl. No.: 11/302,682

(22) Filed: Dec. 13, 2005

(65) Prior Publication Data

US 2007/0136007 A1 Jun. 14, 2007

(51) Int. Cl.
*G01N 33/50* (2006.01)
(52) U.S. Cl. .......................................... 702/23; 436/173
(58) Field of Classification Search .................. None
See application file for complete search history.

(56) References Cited

U.S. PATENT DOCUMENTS

| | | | |
|---|---|---|---|
| 5,470,753 A | 11/1995 | Sepetov et al. | |
| 5,538,897 A | 7/1996 | Yates, III et al. | |
| 6,017,693 A | 1/2000 | Yates, III et al. | |
| 6,489,121 B1 | 12/2002 | Skilling | |
| 6,489,608 B1 | 12/2002 | Skilling | |
| 6,582,965 B1 | 6/2003 | Townsend et al. | |
| 2002/0168682 A1 | 11/2002 | Goodlett et al. | |
| 2003/0028932 A1 | 2/2003 | Skilling | |
| 2003/0228630 A1 | 12/2003 | Tsuda et al. | |
| 2004/0180381 A1 | 9/2004 | Yamaguchi et al. | |

OTHER PUBLICATIONS

Arnott et al. (Electrophoresis, vol. 19, p. 968-980, 1999).*
Bertino et al. (IEEE Transactions on Knowledge and Data Engineering, vol. 1, No. 2, p. 196-214, Jun. 1989).*
Nagarajan et al. (Proceedings of the 30thVLDB Conference, Toronto Canada, p. 1202-1213, 2004).*
Schadforth et al. (Proteomics, 2005, vol. 5, 1787-1796.*

* cited by examiner

*Primary Examiner* — Karlheinz R Skowronek
(74) *Attorney, Agent, or Firm* — Shun Yao; Park, Vaughan, Fleming & Dowler LLP

(57) ABSTRACT

The disclosed technology relates to the creation of creating an indexing system. The indexing system is created by selecting a macromolecule structure and determining a reference mass and an adjacent ion mass. The reference mass and the adjacent ion mass associated with the macromolecule structure are then stored in the indexing system.

11 Claims, 6 Drawing Sheets

METHOD, APPARATUS, AND PROGRAM PRODUCT FOR CREATING AN INDEX INTO A DATABASE OF COMPLEX MOLECULES

CROSS-REFERENCE TO RELATED APPLICATIONS

The subject matter of this application is related to the subject matter in a co-pending non-provisional application by the same inventors as the instant application and filed on the same day as the instant application entitled "Method, Apparatus, and Program Product for Quickly Selecting Complex Molecules from a Database of Molecules," having U.S. Pat. No. 7,429,727, and filing date 13 Dec. 2005.

BACKGROUND

1. Technological Field

The disclosed technology relates to the field of bio-informatics.

2. Background Art

The technology disclosed herein relates to the problems of identifying a macromolecule made up of molecular subunits that are bound at cleavage sites. The identification can be accomplished through the analysis of fragmentation spectra of the macromolecule or of portions of the macromolecule. Such fragmentation spectra can be generated by Tandem Mass Spectrometry ("MS/MS") techniques as are well known in the art.

One skilled in the art will understand that a tandem mass spectrometer generates a fragmentation spectrum containing dissociation spectrum data by selecting charged molecules (the parent ions) that have approximately the same mass-to-charge-ratio "m/z" (generally within a narrow tolerance) in a first stage of the tandem mass spectrometer, causing the selected parent ions to be fragmented at cleavage sites in a second stage, and accumulating the count of the resulting fragments in m/z histogram bins. A number of these bins can represent a single spectral peak. The height, the area, or a combination of the height and area of the spectral peak can be used to calculate the "intensity" of the spectral peak. The dissociation spectrum data making up the fragmentation spectrum from the tandem mass spectrometer can also include the m/z used at the first stage to select the parent ion. The z for the parent ion m/z is often 2 or 3 (thus requiring additional computational overhead for search techniques that use the parent ion mass); the z for fragments of the parent ion generally is 1, which simplifies the determination of the fragment's mass.

The parent ion's mass along with the dissociation spectrum data can be used by well-known sequencing techniques to identify the parent ion. One skilled in the art will understand that if a molecular fragment is singly ionized the mass represents the real mass of the molecular fragment. If the same molecular fragment is doubly ionized, the m/z for that molecular fragment will be ½ the real mass of the fragment.

By identifying parent ions in a database of molecule descriptions one can select descriptions of macromolecules that contain the parent ions.

However, if the tandem mass spectrometer is operated in a "wide-window" mode (thus allowing molecules having significantly different masses to enter the second stage of the tandem mass spectrometer) the resulting dissociation spectrum data will include contributions from fragments of parent ions having different masses. In addition, the masses of the parent ions will be less accurately known. Thus, prior art molecular sequencing techniques that require a substantially exact mass for the parent ion will fail.

All identification techniques use some amount of de novo processing (which processes the dissociation spectrum data without reference to a database of known macromolecules), followed by some amount of database search that compares information gathered from one or more spectra with entries from a database of molecule descriptions. U.S. Pat. No. 5,538,897 to Yates and Eng teaches a nearly pure database search method where the macromolecule is a protein or peptide. Yates computes only a mass for the parent ion from the dissociation spectrum data before referencing the database of molecule descriptions The 'sequence tag' approach of Mann and Wilm (see: *Error-Tolerant Identification of Peptides in Sequence Databases by Peptide Sequence Tags*, Anal. Chem., 1994, 66, 4390-4399) makes greater use of de novo processing than does Yates. In this approach, one or more short subsequences of molecular subunits are computed from the fragmentation spectrum (for example and in the case of a peptide, a subsequence of three consecutive amino acids) and these 'sequence tags' are used to filter entries to find candidates for the parent ion from the database of molecule descriptions. One skilled in the art will understand that candidate entries can be found in the database of molecule descriptions either by a linear search or by an indexed search. The candidate entries found in the database of molecule descriptions can then be scored in detail against the fragmentation spectrum to determine the probability that the entry actually represents the parent ion.

De novo sequencing (see: C. Bartels, *Fast algorithm for peptide sequencing by mass spectrometry*, Biomedical and Environmental Mass Spectrometry 19 (1990), 363-368; and J. Taylor and R. Johnson, *Implementation and uses of automated de novo peptide sequencing by tandem mass spectrometry*, Anal. Chem. 73 (2001), 2594-2605) makes still greater use of de novo processing. It computes one or more hypothetical sequences of molecular subunits that match a fragmentation spectrum. This hypothetical sequence can then be used to filter the database of molecule descriptions, in a style similar to the well-known "BLAST search", to return descriptions of parent ion candidates from the database of molecule descriptions.

Generally, a method using more de novo processing requires a higher quality fragmentation spectrum than does a method using less de novo processing. In particular, de novo processing works very poorly with mixture spectra, that is, fragmentation spectra resulting from fragments of more than one parent ion. On the other hand, a method using more de novo processing is generally faster, because it returns fewer descriptions of candidates for the parent ion, and is generally more robust to discrepancies between the macromolecules represented by the fragmentation spectrum and the descriptions of known molecules in the database. Discrepancies can include database errors, polymorphic molecules, modified molecules, molecules bound to salt ions, and many other possibilities.

In all three approaches (database search, sequence tag search and de novo sequencing) the database of molecule descriptions is filtered to return descriptions of macromolecules that could represent the parent ion. This reduces the number of candidate descriptions that need to be processed by a computationally expensive scoring procedure.

The mass of a parent ion is a very weak filter for a database of peptides. For ion-trap instruments, the parent mass is typically known to within a range of about 3 Daltons (for more accurate instruments, due to the clustering of peptide masses, this value may still be known only to the closest integer). With a 3-Dalton range, each residue in a peptide has about a 3% chance of completing a peptide that fits the parent ion's mass (because residues average about 100 Daltons). Thus accessing a 1-billion-residue database of peptide descriptions by the mass of the parent ion will return 30 million candidates, each of which needs to be scored. Thus, the processing time available severely limits the complexity of the scorer.

A three letter sequence tag (for example, in a peptide a sequence of three amino acids) is a much stronger filter for a database of peptides than the mass or mass of a parent ion. Each residue in a peptide has about a 0.013% chance of completing a given three-letter tag (about 1 chance in 20 for each of the three letters, so 1/(20*20*20) chance overall). Thus, using a sequence tag as a filter returns 130,000 candidates from the 1-billion-residue database instead of 30 million candidates as returned using the mass of a parent ion as a filter. However, it is difficult to compute a three-letter 'sequence tag' (especially if the provided spectrum is of poor quality, or if the provided spectrum is of a mixture of parent ions).

The article (Tang et al. *Discovering known and unanticipated protein modifications using MS/MS database searching*, Analytical Chem. 77 (2005), 3931-3946) teaches an indexing method using single predicted peaks along with the parent ion mass. This approach does not provide a sufficiently powerful filter for wide-window spectra data acquisition.

There exists a need for a faster, more sensitive and more robust way to select descriptions of candidate parent ion descriptions from a database of molecule descriptions.

DETAILED DESCRIPTION

Figure 1:
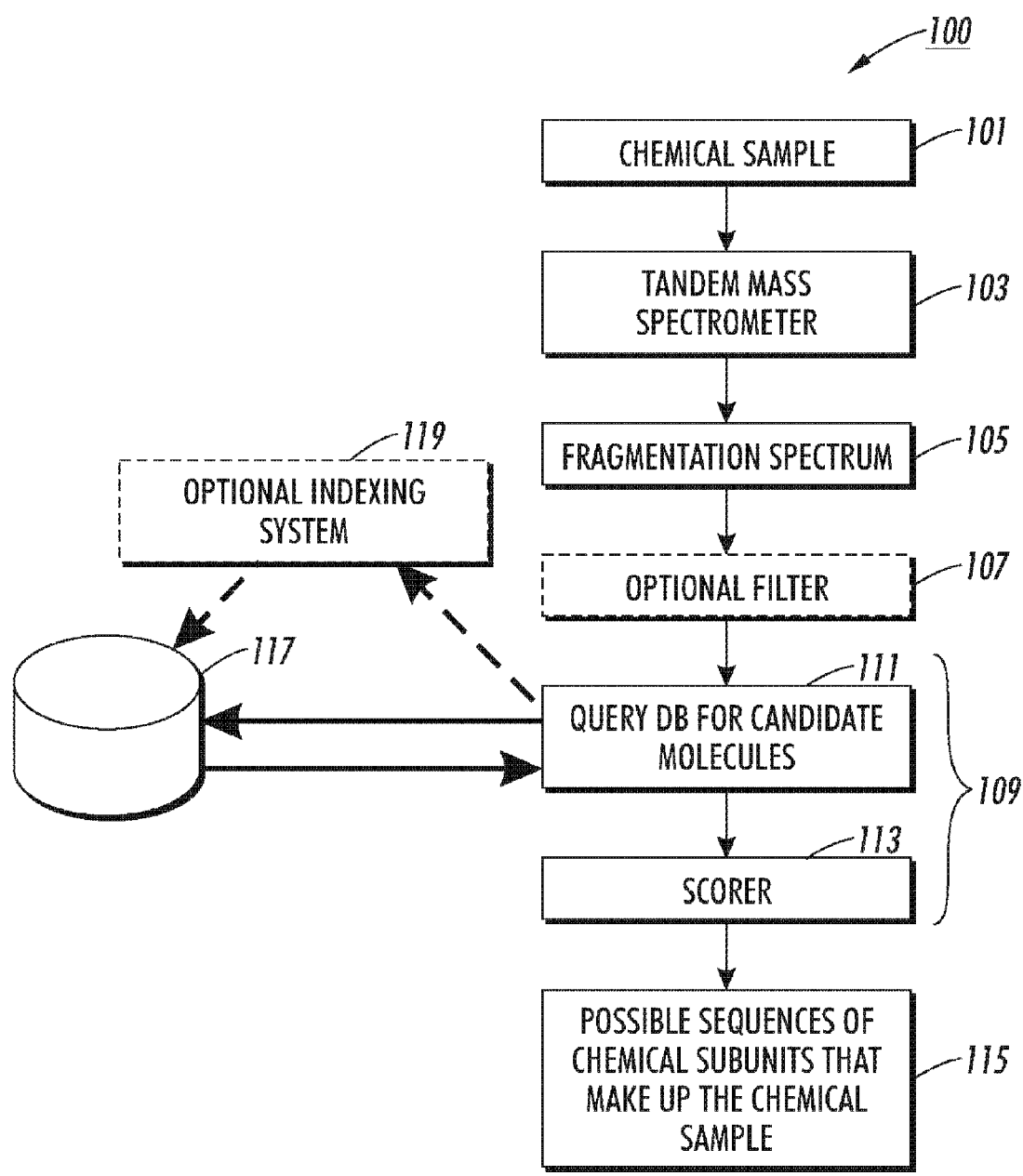
FIG. 1 Illustrates a molecular sequencing system.

The disclosed technology teaches new ways of selecting descriptions of candidate molecules from a database of molecule descriptions. The technology uses a mass to filter entries from the database of molecule descriptions. Thus, in the case of peptides, instead of requiring that an amino acid string be identified from the dissociation spectrum data and used to locate peptide descriptions in a protein database, an query peak (I) is identified in the dissociation spectrum data and the filter returns, as candidate parent ion descriptions, all peptide descriptions in the protein database that have a predicted b-ion or y-ion peak at I and that have a total mass in approximate agreement with the mass of the spectrum's parent ion. A refinement of this technology determines a query pair (IJ) from the dissociation spectrum data where J minus I is equal to an amino acid residue mass (rounded to an integer). The database of molecule descriptions can be filtered to find macromolecule descriptions having a peak pair (IJ)that matches the query pair (IJ) as either successive b-ions or successive y-ions. One skilled in the art will understand that multiple query pairs (IJ) or multiple query peaks (I) would improve the strength and sensitivity of the filter. For example, powerful filtering is obtained by requiring that non-tryptic peptides match two out of ten query pairs (IJ) and that tryptic peptides match one out of ten query pairs (IJ).

One skilled in the art will understand that in the case of peptides and for b- and y-ions (prefixes and suffixes), ion masses are computed by summing amino acid residue masses along with an extra proton on the b-ion and an extra water and proton on the y-ion.

This technology has some similarities with the 'sequence tag' approach for peptides, but does not require an identification of a string of three or four amino acids (or other molecular subunits). Instead (for peptides), any string of amino acids that combine to have a computed ion mass of I may be returned from the database of molecule descriptions.

One aspect of the disclosed technology is related to the analysis of dissociation spectrum data that includes spectral peaks that represent fragments of a parent ion. The parent ion includes molecular subunits that are connected at cleavage sites. The technology accesses the dissociation spectrum data and determines a reference mass (to be used in database queries) of one of the fragments where at least one of the molecular subunits in the fragment is unknown. The technology also selects a description of a candidate parent ion description from a database of molecule descriptions where a computed ion mass of the candidate parent ion description matches the reference mass and scores the candidate parent ion description for how well an embodiment of the candidate parent ion description matches the dissociation spectrum data.

Another aspect of the disclosed technology is that of creating an indexing system. The indexing system maps index peak pairs (IJ) to residue positions within macromolecule descriptions in the database of molecule descriptions. The I is a reference mass and (J minus I) is an adjacent residue mass. Thus, the computed index peak pair (IJ) represents the mass of a first ion (I), and the mass of an adjacent ion mass (J) where (J) is equal to (I) plus the mass of a molecular subunit. For example in proteomics, (I) represents the mass of a sequence of amino acids where at least one amino acid in the sequence is not known and (J) represents the mass of (I) plus the mass of any other amino acid residue. In one embodiment, these masses are represented by integers. The index peaks (I) or the index peak pairs (IJ) for the database of molecule descriptions can be used to match query peaks (I) or query pairs (IJ) found in a fragmentation spectrum through a linear search of the database of molecule descriptions or, in the case of query pairs (IJ), through an indexed search via the indexing system.

Another aspect of the technology is a computer-usable data carrier having a data structure embodied within that includes an indexing system for accessing a database of molecule descriptions. The indexing system includes ordered pairs organized into a list. The ordered pairs include a reference mass and an adjacent ion mass, the ordered pairs used to locate one or more macromolecule entries from the database of molecule descriptions. The located macromolecule entries including descriptions of molecular subunits having computed ion masses that match the reference mass and the adjacent ion mass.

While much of the following description of the technology is presented in the context of protein analysis, the disclosed techniques can be used to filter descriptions of other macromolecules so long as the described macromolecules are made up of molecular subunits bound together at cleavage sites. One skilled in the art will also understand that the database of molecule descriptions includes descriptions of the molecules and not the molecules themselves. Thus, while that actual molecules are fragmented by the tandem mass spectrometer, the actual molecules are represented in a database using a description. The description provides data about the described molecule that can be used to calculate the computed ion mass of the described molecule. The specification sometimes uses molecule with reference to a database. One skilled in the art will understand from the context that the reference is to a description of the molecule and not to any specific instantiation of a molecule having that description.

A query peak (I) can be generated from a fragmentation spectrum and, in proteomics, represents the mass of a b- or y-ion. A query pair (IJ) can be generated from a fragmentation spectrum and, in proteomics, can represent the mass of a b-ion and the mass of a subsequent b-ion. For example, for the peptide AEFVEVTK, if I is the mass of the b3 ion (prefix AEF) then J would be the mass of the b4 ion (AEFV). In some embodiments the I and J values each represent the mass of their respective ion to integer accuracy.

FIG. 1 illustrates operation of a molecular sequencing system 100. In such a system, a chemical sample 101 is input to a tandem mass spectrometer 103 that generates a fragmentation spectrum 105 (see FIG. 3). The fragmentation spectrum 105 can be processed by an optional spectrum filter 107 that passes high quality spectra to a sequencer 109. The sequencer 109 processes the fragmentation spectrum 105 to determine a possible sequence of chemical subunits 115 that make up the chemical sample 101. The sequencer 109 can include a 'query DB for candidate molecules' procedure 111 that initially selects descriptions of molecules that can match the characteristics of the fragmentation spectrum 105. The description of these initially selected molecules can then be passed to a 'score candidate molecules' procedure 113 that analyzes the descriptions of the initially selected molecules to find which of the molecules best match the characteristics of the fragmentation spectrum 105. The descriptions of the initially selected molecules are stored in a database of molecule descriptions 117. The 'query DB for candidate molecules' procedure 111 can search the database of molecule descriptions 117 using a linear search or an optional indexing system 119. The linear search and indexed search are subsequently described.

Either one or more query peaks (I) or query pairs (IJ) can be used by a linear search through a database of molecule descriptions to filter descriptions from the database of molecule descriptions 117 for analysis. One skilled in the art will understand that generally searches (whether a linear search or an indexed search) will search for multiple queries during a single traversal of or reference to the database of molecule descriptions. The multiple queries can result from a single fragmentation spectrum or from a collection of fragmentation spectra.

The query pair (IJ) can be used as an index into the database of molecule descriptions 117 by matching an index peak pair (IJ) into the database of molecule descriptions 117. One aspect of the disclosed technology teaches a process that creates an indexing system for the database of molecule descriptions 117 where the query pair (IJ) entry indexes, for example, to peptide P if P includes the index peak pairs (IJ) as successive b-ions or successive y-ions. Similar processing can be done for analogous macromolecules. This technology can use index peak pairs (IJ) to build the index for the database of molecule descriptions 117, and it can use query pairs (IJ) to query the database of molecule descriptions 117 using the index.

The database of molecule descriptions 117 and/or the optional indexing system 119 can be provided and/or accessed over a network or other computer-usable data carrier; can be stored on and/or accessed from a storage system, and/or accessed directly from the computer-usable data carrier.

Figure 2:
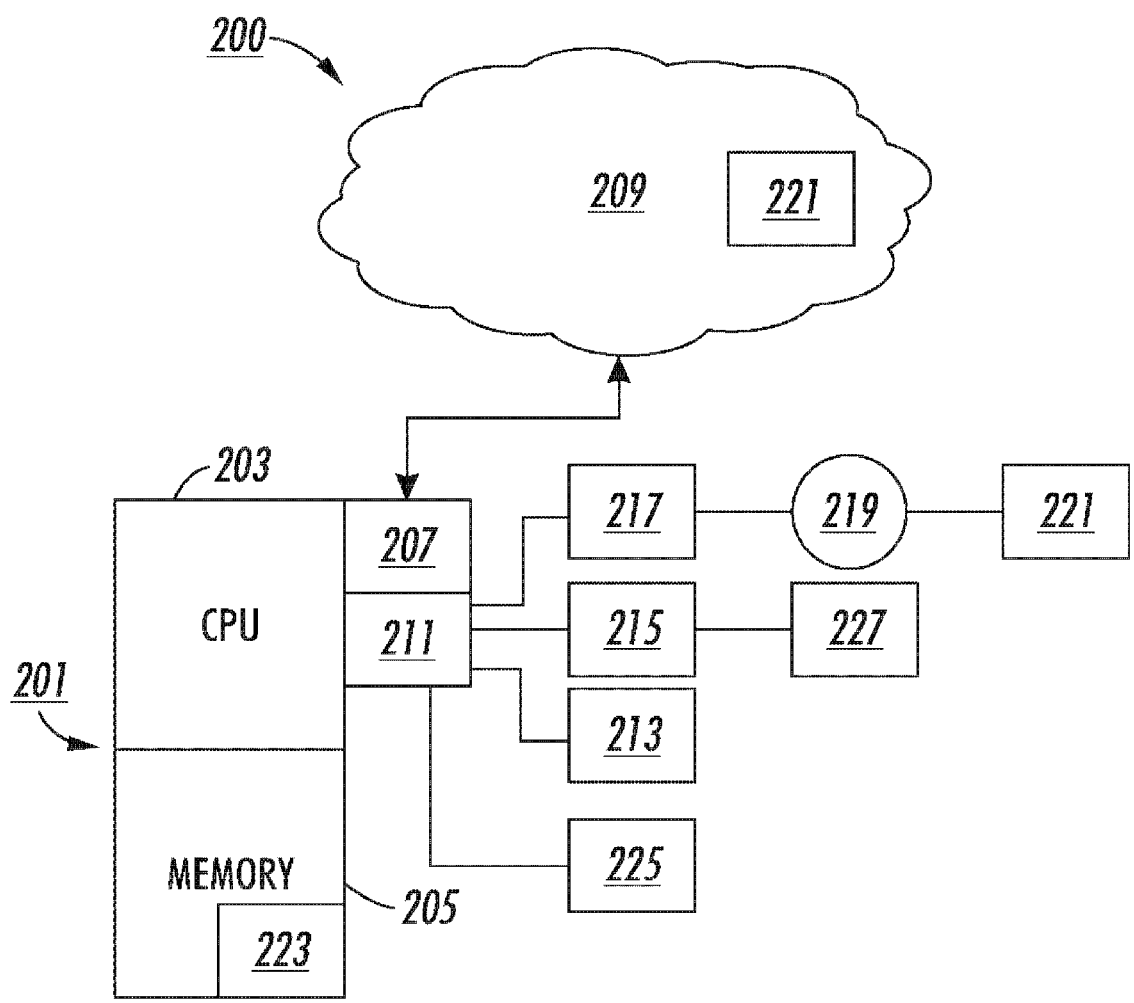
FIG. 2 illustrates a computer system in accordance with a preferred embodiment.

FIG. 2 illustrates a computer system 200 that can incorporate the disclosed technology. The computer system 200 includes a computer 201 that incorporates a CPU 203, a memory 205, and, in some embodiments, a network interface 207. The network interface 207 provides the computer 201 with access to a network 209. The computer 201 also generally includes an I/O interface 211 that can be connected to a user interface device(s) 213, a storage system 215, and a removable data device 217. The removable data device 217 can read a tangible computer-usable data carrier 219 that typically contains a program product 221 that incorporates the technology disclosed herein. The storage system 215 (along with the removable data device 217), the tangible computer-usable data carrier 219 and any network file storage comprise a file storage mechanism. The tangible computer-usable data carrier 219 can be a ROM within the computer system 200, a replaceable ROM, a memory stick, CD, floppy, DVD or any other tangible media. The program product 221 accessed from the tangible computer-usable data carrier 219 is generally read into the memory 205 as a program 223 that instructs the CPU to perform the processes described herein as well as other processes.

A tandem mass spectrometer 225 can be in direct communication with the I/O interface 211 and can provide dissociation spectrum data directly to the computer 201 (for example, by using a data bus such as a SCSI, USB, FireWire®, custom or other connection). In addition, the tandem mass spectrometer 225 can provide dissociation spectrum data over the network 209, or via the tangible computer-usable data carrier 219. One skilled in the art will understand that not all of the displayed features of the computer 201 need to be present for all embodiments.

A database of molecule descriptions 227 can reside on the storage system 215 for access by a linear search or an indexed search as is subsequently described.

Figure 3:
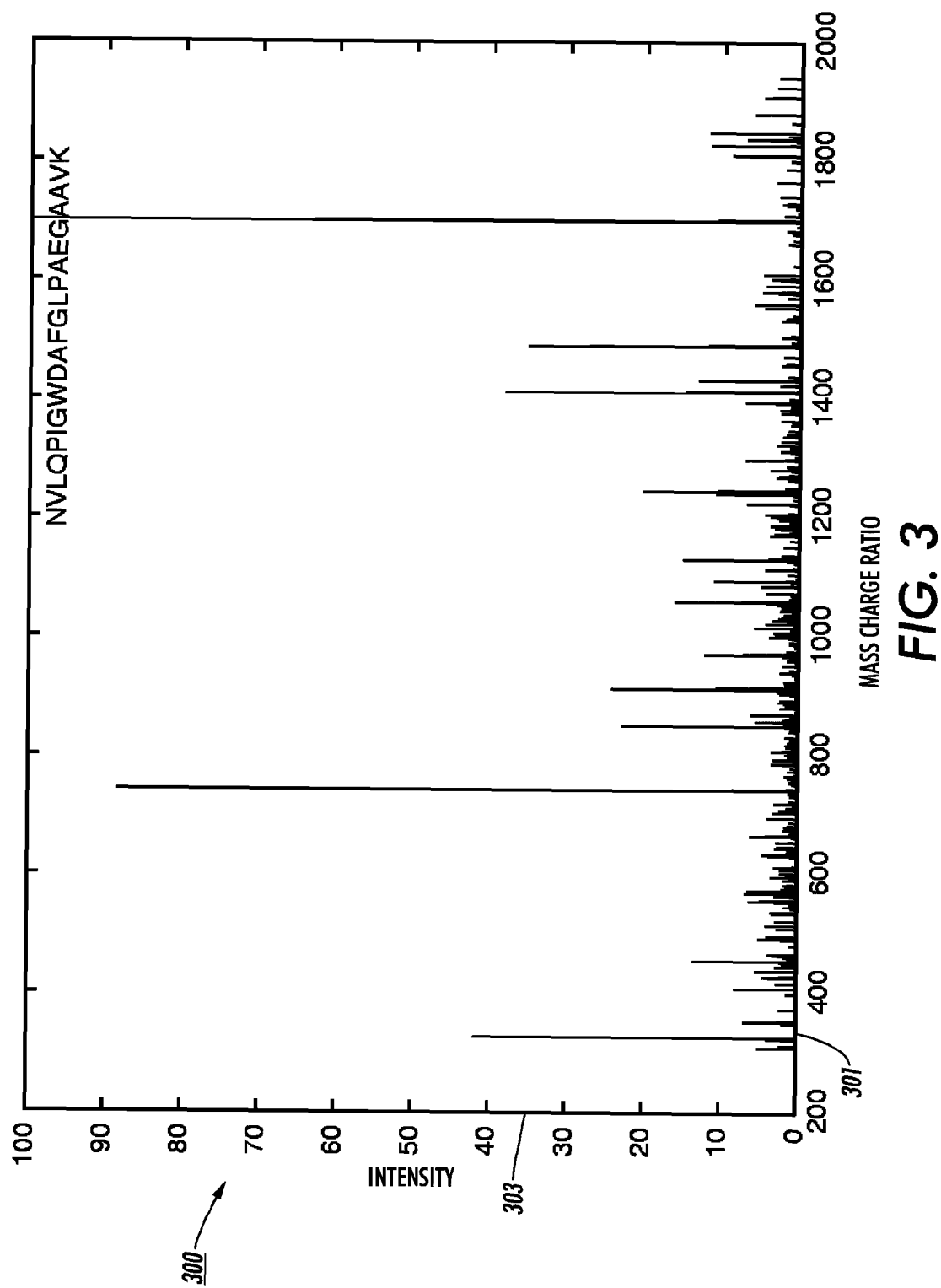
FIG. 3 illustrates a histogram of an example fragmentation spectrum that can be produced by a tandem mass spectrometer and that indicates the number of ions observed at each binned mass.

FIG. 3 illustrates an example tandem mass spectrometer fragmentation spectrum 300 of a parent ion plotted on an x-axis in m/z 301 and a y-axis in intensity 303. The parent ion (in this case a peptide) includes a number of molecular subunits (in this case amino acids) connected at cleavage sites. The tandem mass spectrometer dissociates many of the parent ions into at least two fragments at any of the cleavage sites. The intensity of a spectral peak indicates how often the parent ions have been fragmented at a particular cleavage site. One skilled in the art will understand that the x-axis in m/z 301 of the fragmentation spectrum is a measurement of the ion's mass divided by the charge on the ion. Generally most peptide fragments are singly charged. Hence, the measurement is equivalent to the mass of the ion.

The parent ion may be a protein, peptide, lipid, polymer (composed of multiple monomers), glycan, etc. Much of the rest of this description is cast in the context of peptides and amino acids. However, one skilled in the art will understand that the techniques taught herein can be applied to other molecules that have molecular subunits connected by cleavage sites.

One difficulty with dissociation spectrum data is that it is very difficult to distinguish noise peaks from useful spectral peaks. In the case of peptides and proteins, it is also very difficult to determine which spectral peaks indicate b-ions, y-ions, a-ions, or noise. These difficulties increase the complexity of analyzing dissociation spectrum data to determine the sequence of molecular subunits that make up the parent ion. This difficulty has been traditionally addressed by assuming the parent ion mass provided by the tandem mass spectrometer is correct within a small tolerance, or by detecting a 'sequence tag' from the dissociation spectrum data and not using the provided parent ion mass at all. The inventor uses the parent ion mass with a wide tolerance with either a query peak (I) or query pair (IJ) to search the database of molecule descriptions for candidate molecules for scoring. This technique enables detection of candidates that will match mutations or modifications of the parent ion.

The inventor has realized that good database filtering can be accomplished by using the mass of a spectral peak from the fragmentation spectrum (a query peak (I)) to select entries from a database of molecule descriptions instead of using the mass differences of the spectral peaks in the fragmentation spectrum. The inventor has also realized that extremely good database filtering can be accomplished by using a query pair (IJ) to select entries from a database of molecule descriptions. The query pair (IJ) is determined from the dissociation spectrum data by assigning the mass of one spectral peak to I, detecting the existence of a spectral peak at J where J is the sum of I and the computed ion mass of any single molecular subunit. Thus, in the case of proteins, I would be the mass of some string of amino acids while J is I plus the mass of an amino acid that immediately follows the string of amino acids represented by I. Thus, instead of matching the mass of the parent ion (within a small tolerance); or identifying a 'sequence tag' of 3 or 4 sequential amino acids from the dissociation spectrum data and determining a flanking mass on either or both sides of the 'sequence tag'; the technology disclosed herein uses a query peak (I) to filter (select) a description from the database of molecule descriptions where the query peak (I) matches the computed mass of a string of molecular subunits (the index peak (I). Some embodiments also impose the constraint that the query peak (I) be followed by another peak having the mass of the query peak (I) plus the mass of a single known molecular subunit (thus, a query pair (IJ)). In some embodiments, the parent ion mass can also be used with the query peak (I) or the query pair (IJ) to filter the candidate molecules.

In some embodiments possible entries can be selected from a database of molecule descriptions using the query peak (I) or query pair (IJ) by a linear search through the database of molecule descriptions. It has been found useful to illustrate the technology with an example. The following assumptions are used to simplify the example. Assume the database of molecule descriptions contains a single "protein" as the macromolecule. Assume that the macromolecule includes one million amino acid residues (the molecular subunits). Assume the tandem mass spectrometer is configured to provide a spectrum for parent ions having a m/z in the range of 1400 to 1500. Further assume that a resulting fragmentation spectrum produces a query pair (IJ) of (500, 613).

The description of the protein in the database of molecule descriptions will contain approximately 20,000,000 peptide combinations (assuming only peptides having a length of 10-30 amino acids—a typical range for proteomics). Of these 20,000,000 peptides, approximately 1,000,000 will be peptides having a parent ion mass in the range of 1400 to 1500.

One embodiment using the disclosed technology is a linear search process used to filter the database of molecule descriptions for peptides. This embodiment establishes a "window" that contains a subsequence S of amino acids that have a total mass M. If M exceeds 1500, the left edge of the window is advanced to reduce the subsequence S by one amino acid and the mass of the removed amino acid is subtracted from M. If M is less then 1400, the right edge of the window is advanced to increase the subsequence S by one amino acid and the mass of the added amino acid is added to M.

If M falls in the range 1400 to 1500, the process counts how many query pairs (IJ) and/or query peaks (I) from the dissociation spectrum data match the computed ion masses of strings of amino acids (the index peak pairs (IJ) or index peaks (I)) in the subsequence S.

The computed b-ion masses in S can be determined by summing the masses of each prefix subsequence of amino acids (and adding 1 for the mass of a proton). Computed y-ion masses in S can be determined by summing the masses of each suffix subsequence of amino acids (and adding 19 for the mass of water and a proton). A number of optimizations known to one skilled in the art to speed execution can be applied. For example, if the parent mass range is large it is advantageous to check for query matching before checking the parent ion mass.

The reason why the query peak (I) and query pair (IJ) are such strong filters for selecting descriptions of macromolecules is now described in the context of proteins. At any single residue A in the database of molecule descriptions, a peptide extending to the right (towards the C-terminus) from A matches a query pair (IJ) with probability about 1/1800, because the chance of matching query peak (I) is about 1 in 100 (since residues have average mass about 100), and the chance of matching J given a match to query peak (I) is about 1 in 18. Thus requiring a single query pair (IJ) hit on a single trial reduces the number of candidate peptides from about 1 million (the total number of peptides with mass in the range [1400, 1500]) to about 600 (1,000,000/1800). By requiring two hits out of ten trials, or three hits out of 15 trials, and allowing either b-ion hits or y-ion hits, the number of candidate peptides to be passed to the 'score candidate molecules' procedure 113 can be adjusted (tuned) to a desired time budget. One skilled in the art will understand that "two hits out of ten trials" terminology refers to providing ten query pairs (IJ) or ten query peaks (I) and requiring that each returned candidate contain at least two of the ten. The required number of hits may differ if the peptide ends in R or K (and/or begins after an R or K), which is indicative of a tryptic peptide. A scorer that makes the final selection from the list of candidate molecule descriptions is typically fast enough to score 50,000 candidates per second on contemporary desktop computers if seeking an exact match, and perhaps 5000 candidates if seeking a match to a modification or mutation. The molecular sequencing system 100 can be tuned by changing the constraints of the candidate selection to match the speed of the 'score candidate molecules' procedure 113.

Figure 4:
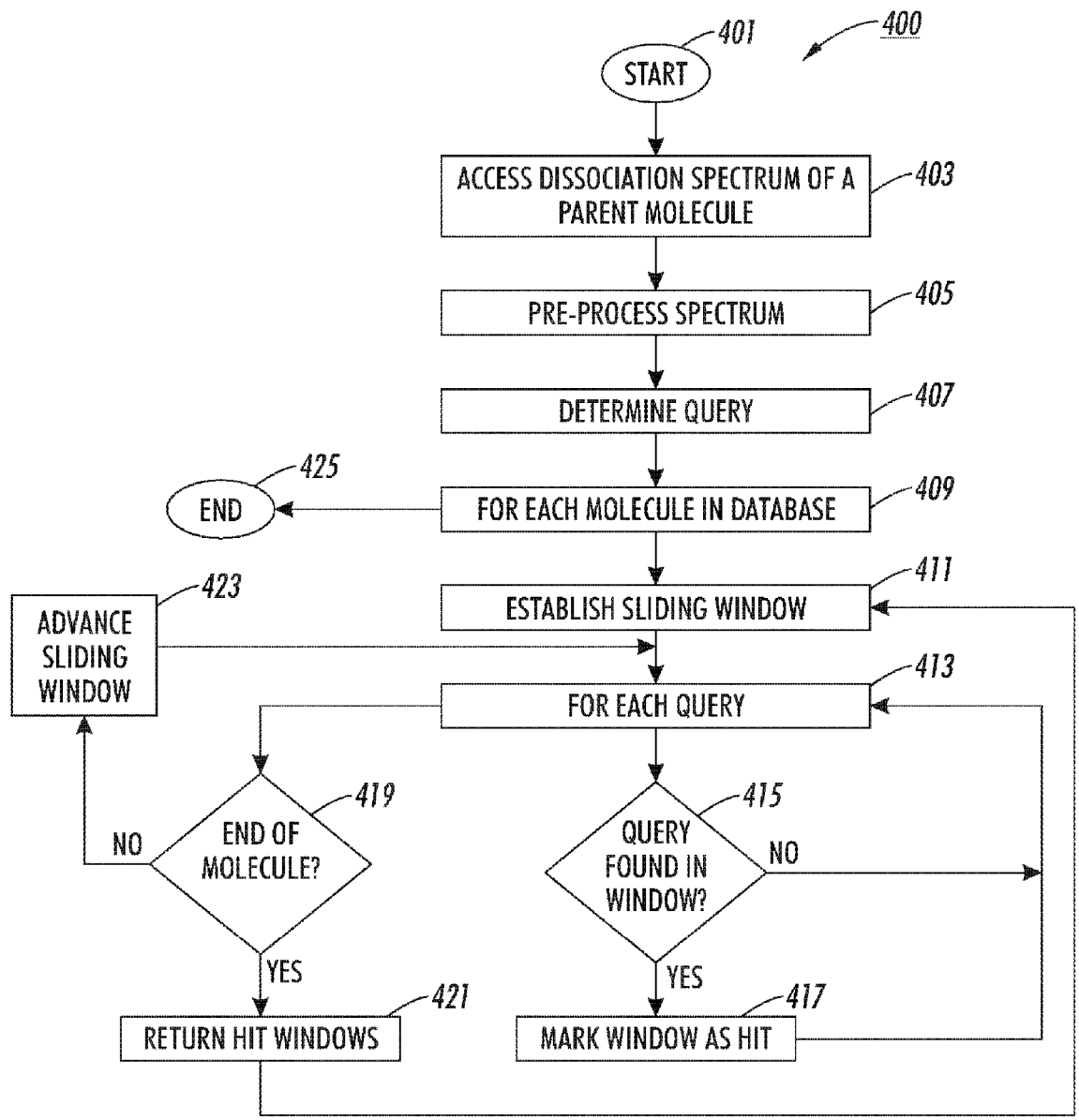
FIG. 4 illustrates a molecular candidate selection process.

FIG. 4 illustrates a molecular candidate selection process 400 that shows one embodiment of the disclosed technology. The molecular candidate selection process 400 can be invoked for one or more of the accessed fragmentation spectra. The molecular candidate selection process 400 can be implemented as a programmed-procedure, a task, a thread, or (if implemented by dedicated circuitry or processor),through the use of, for example, an API, device driver, or other interface. One embodiment contemplated by the inventors includes an array of dedicated processors each configured to perform the molecular candidate selection process 400.

The following description is directed towards the detection of a query pair (IJ) in the database of molecule descriptions. However, one skilled in art after reading the description herein, would understand how to modify the described technology to use query peaks (I) to select candidate macromolecules (such as proteins and/or peptides).

The molecular candidate selection process 400 initiates at a 'start' terminal 401 and continues to an 'access spectrum' procedure 403 that accesses the fragmentation spectrum directly or indirectly (such as by reading a file that contains the fragmentation spectrum data) from a tandem mass spectrometer or equivalent system. The spectrum can be preprocessed by a 'preprocess spectrum' procedure 405 that, for example, can adjust the intensities of the peaks responsive to the mass relationships between the peaks, consolidates and/or removes isotope peaks and or water loss peaks, detects and compensates for multiply charged ions, and other adjustments known to one skilled in the art. The molecular candidate selection process 400 continues to a 'determine query' procedure 407 that selects peaks that are candidates for designation as a query peak (I) or an query pair (IJ). This selection can be performed by ordering spectral peaks by intensity, selecting a peak from the set of ordered peaks, and determining whether significant peaks exist at the 18 possible masses (representing the masses of the amino acids) greater than the mass of the selected peak. If the selected peak is followed by a peak having a mass of the selected peak plus the mass of an amino acid, the mass of the selected peak is set as the reference mass (the query peak (I)) and a query pair (IJ) is determined for each significant peak located at one of the possible 18 amino acid masses larger than the reference mass. In addition, the spectrum is examined for peaks at the 18 masses less than the selected peak. If the selected peak is preceded by a peak having the mass of the selected peak minus the mass of an amino acid, the mass of the preceding peak is set as the reference mass (the query peak (I)) and the mass of the selected peak is set as the J of the query pair (IJ). Duplicated query values, if any, are removed from the list.

At this point, a suitably sized set of query peaks (I) or query pairs (IJ) has been extracted from the dissociation spectrum data representing the fragmentation spectrum and the molecular candidate selection process 400 continues to an 'iterate molecule' procedure 409 that iterates through each macromolecule contained in a database of molecule descriptions. As each macromolecule is iterated, an 'establish window' procedure 411 establishes a sliding window that starts at one end if the macromolecule and slides to the other end. Where the iterated macromolecules are proteins, and the spectra are of peptide fragments (or for any similar macromolecule arrangement), the window can contain both b-ions and y-ions. In some embodiments one or both edges of the window can be repositioned or moved independently. Thus, the size of the window can change.

Once the window is established, the molecular candidate selection process 400 continues to an 'iterate each query' procedure 413 that iterates each query peak (I) or query pair (IJ). For each iterated query, a 'query found in window' decision procedure 415 determines whether the window contains a sequence of molecular subunits having masses that sum to the reference mass, followed by a single molecular subunit such that the reference mass plus the mass of the molecular subunit is that of the adjacent ion mass (where the query is a query pair (IJ); if the query is a query peak (I) the determination is whether the window contains a sequence of molecular subunits having masses that sum to the reference mass). If this condition does not exist, the molecular candidate selection process 400 continues to the 'iterate each query' procedure 413 to iterate the next query for the window. The sum of the molecular subunit masses is the computed ion mass for that sequence of molecular subunits.

If, at the 'query found in window' decision procedure 415, a match is found the molecular candidate selection process 400 continues to a 'mark window' procedure 417 that marks the window as having a hit (that is, that an iterated query matched some sequence in the window, and maintaining a count of hits for that window). A window that has at least one hit is a marked window.

After all the queries are iterated, the molecular candidate selection process 400 continues to an 'end of molecule' decision procedure 419 that determines whether the end of the macromolecule has been reached. If so, the molecular candidate selection process 400 continues to a 'return hit windows' procedure 421 that can return the marked windows that have a number of hits that satisfy a threshold (the threshold can be one), the description of the macromolecule containing the window, and the number of times the window was hit for that macromolecule. Then the molecular candidate selection process 400 can continue to the 'iterate molecule' procedure 409 to iterate the next macromolecule description.

However, if at the 'end of molecule' decision procedure 419, the end of the macromolecule has not been reached, the molecular candidate selection process 400 continues to an 'advance window' procedure 423 that advances (or repositions) at least one edge of the window. The window's edges are repositioned as appropriate for the matching algorithm. Once the window's edge is repositioned, the molecular candidate selection process 400 continues back to the 'iterate each query' procedure 413 to detect and register query matches in the new window.

After the last macromolecule has been iterated by the 'iterate molecule' procedure 409, the molecular candidate selection process 400 completes through the 'end' terminal 425.

Another embodiment of the molecular candidate selection process 400 receives query peaks (I) or query pairs (IJ) from a plurality of fragmentation spectra and tracks which results are associated with which fragmentation spectrum. One skilled in the art, after reading the description herein would be able to implement such an embodiment without undue experimentation.

At the completion of the molecular candidate selection process 400, a selection of macromolecule descriptions have been identified from the database of molecule descriptions that are good candidates for further analysis and scoring to identify the sequence of molecular subunits in the parent ion. In some embodiments the 'score candidate molecules' procedure 113 is tolerant to modifications, mutations and database errors.

In one embodiment, the edges of the window are separately controlled. Further, leading and trailing ion selections can be determined from the appropriate side of the window (in the proteomics case, this helps determine b-ions and y-ions).

The procedures described above can be implemented by logic such as an input logic, a determination logic, a selection logic, a scoring logic, a search logic, an indexing system, an index output logic, storage logic, and database output logic; such logic and systems can be implemented using electronic circuits, programs on a computer, or some combination of these or similar approaches known to one in the art.

TABLE 1 lowest-parent = lowest parent ion mass we want to consider
highest-parent = highest parent ion mass we want to consider
window-mass = mass of peptide in current window
Do {
   while (window-mass < lowest-parent) {
      advance right edge of window
      update window-mass};
if (window-mass>=lowest-parent && window-mass<=highest-parent){
   check for (i, j) hits;
   if (# hits is large enough){
      add window peptide to candidate list};

TABLE 1-continued

```
    save left edge of window as L;
    advance left edge of window;
      update window-mass;
    while (window-mass >= lowest-parent){
      check for (i, j) hits;
      if (# hits is large enough){
        add window peptide to candidate list};
      advance left edge of window;
      update window-mass};
    restore left edge of window to equal L;
    advance right edge of window;
    update window-mass};
  if (window-mass > highest-parent){
    advance left edge of window
    update window-mass}
} until end of molecule
```

Table 1 contains pseudocode that represents one embodiment of the windowing aspects of FIG. 4.

Using an indexed search instead of a linear search can greatly reduce the time required to select candidate parent ion descriptions from the database of molecule descriptions. One embodiment of an indexing system for a protein database comprises two lists for each index peak pair (IJ), one list for b-ions and the other list for y-ions. There are approximately 36,000 distinct index peak pairs (IJ), as there are approximately 2000 different I values and 18 different (J minus I) values (the 18 amino acid unique masses). Each list element contains an identifier into the database of molecule descriptions. The identifier can be, for example but without limitation, a pair identifying the protein and an endpoint of a peptide within that protein containing a string of amino acids with computed ion masses that match the index peak pair (IJ). It is convenient that the index peak pairs (IJ) for b-ion strings point to the b-ion strings' left endpoints and to the y-ion strings' right endpoints.

The memory requirements of such an indexing system is large. Each amino acid residue in the database will receive about 40 pointers, one for each b-ion pair extending to the right and one for each y-ion pair extending to the left. The memory requirements of an index containing single peaks (index peaks (I) rather than a index peak pair (IJ)) or containing parent ion masses (as taught in Tang et al.) would be similarly large, and because there are fewer lists, each list would be correspondingly larger, which degrades the running time of retrieval by index. The use of index peak pairs (IJ) as the indices into the database, increases the performance of accessing the database of molecule descriptions through the indexing system. Those skilled in the art would use standard techniques, for example, "delta encoding" of protein numbers, or parallel processing, to reduce the sizes of the index or indexes; or the time to access the candidate parent ion description.

Finally, note that within a given mass range, the number of tryptic peptides (corresponding to the specific cleavage of the enzyme trypsin) is about 100 times smaller than the total number of peptides, and hence the indexing system is very useful (from an index size perspective) for "preferred" peptides. An indexing system for a general database of molecule descriptions may be optimized to allow different indexing systems for different families of macromolecules (such as species-specific molecules, or molecules that have a particular characteristic). Thus, the disclosed technology provides the ability to maintain a single large protein database (such as SwissProt or NCBI Non-Redundant), but "swap in" an indexing system for the specific species (such as Human) under study.

Figure 5:
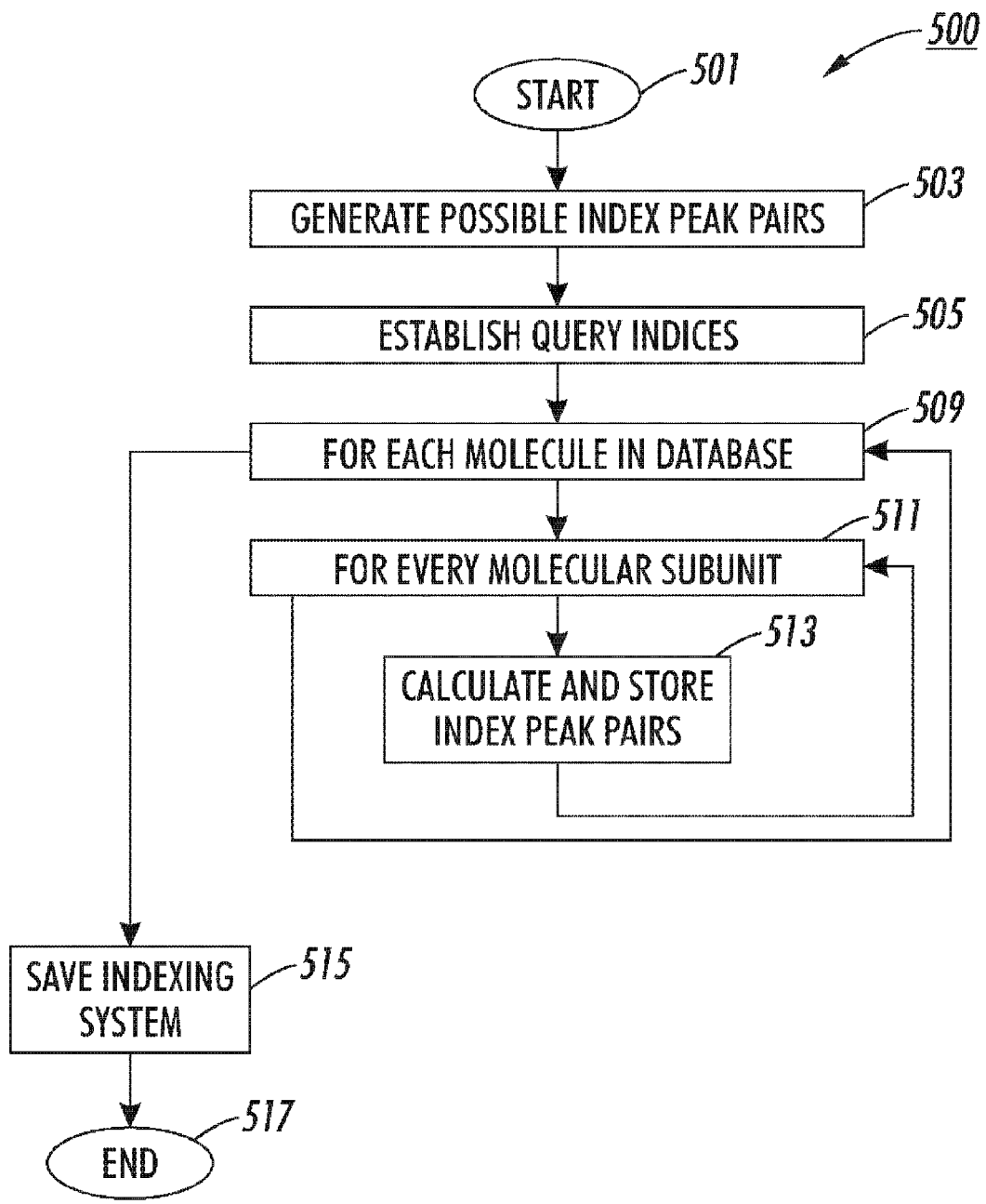
FIG. 5 illustrates a process for constructing an index into a database of molecule descriptions.

FIG. 5 illustrates an index construction process 500 that can be performed for any particular database of molecule descriptions to generate data for an indexing system. The index construction process 500 generates index peak pair (IJ) indices into the database of molecule descriptions to more quickly locate the molecular subunit sequences that match the query pairs (IJ) extracted from dissociation spectrum data. The index construction process 500 can be provided as a program that accepts the database of molecule descriptions and generates the indexing system into the database of molecule descriptions for all entries in the database of molecule descriptions or for any selected portion(s) of the database of molecule descriptions (thus, for example, a very large multi-species database of molecule descriptions can have separate indexing systems for human proteins, mouse proteins, and/or any union or join of the proteins). The indexing system can also be provided with, or be incorporated into, the database of molecule descriptions. Some embodiments of the index construction process 500 can be implemented using special purpose circuitry alone and/or in conjunction with a programmable processing unit. Other embodiments allow the addition of additional molecules to the indexing system (thus allowing the combination of two or more molecular databases within the same indexing system. The query pairs (IJ) are calculated using the computed ion mass of portions (or the entirety) of the described molecule.

The index construction process 500 initiates at a 'start' terminal 501 and continues to a 'generate possible index peak pairs (IJ)' procedure 503 that generates all possible index peak pairs (IJ) given the characteristics of the expected fragmentation spectrum and the characteristics of the molecular subunits as described by the entries in the database of molecule descriptions.

As previously described, if measuring proteins or peptides, there are approximately 36,000 possible index peak pairs (IJ) for a typical range of I and J. The index peak pairs (IJ) can be generated algorithmically, or generated once and accessed from a storage for subsequent use by the indexing system. Once the index peak pairs (IJ) in the database of molecule descriptions have been identified, an 'establish query indices' procedure 505 can generate one or more indices that will contain 'locator data' into the database of molecule descriptions for each possible index peak pair (IJ). One skilled in the art will understand that an associative array, a hash mechanism, or any other technique known in the art, can be used to enable the index peak pair (IJ) to be used as an index to access 'locator data' that references one or more entries in the database of molecule descriptions.

Once the possible index peak pairs (IJ) have been determined and the index peak pairs (IJ) indices established, an 'iterate molecule' procedure 509 iterates each relevant entry in the database of molecule descriptions. In some embodiments, every entry in the database of molecule descriptions will be relevant. In some embodiments, only those entries having particular characteristics will be relevant (for example, only macromolecule descriptions from a specific species, etc.). For each iterated macromolecule description, an 'iterate molecular subunits' procedure 511 iterates a molecular subunit description (for example, by iterating an index into the macromolecule description to specify a specific molecular subunit and/or mass of a specific molecular subunit). In addition, if the indexing system is specific to tryptic peptides, then only molecular subunit descriptions consistent with the cleavage action of the trypsin enzyme will be iterated.

For each iterated molecular subunit description, a 'calculate and store index peak pairs (IJ)' procedure 513 can compute the index peak pair (IJ) values by summing the mass of prefixes and suffixes of the iterated molecular subunit description (if the macromolecule is a protein, the prefix and suffix sums correspond to computed ion masses of b-ions and y-ions). For each computed index peak pair (IJ) the 'locator data' identifying the right and left portion of the molecular subunit description in the database of molecule descriptions is stored and associated with the corresponding index peak pair (IJ). Some embodiments limit the value of the computed I and J to a maximum and minimum mass range.

After all the index peak pairs (IJ) and 'locator data' related to the iterated molecular subunit have been stored for the molecular subunit, the index construction process 500 returns to the 'iterate molecular subunits' procedure 511 to iterate the next molecular subunit description until the macromolecule description iterated by the 'iterate molecule' procedure 509 is completely processed. When the macromolecule description is completely processed, the index construction process 500 returns to the 'iterate molecule' procedure 509 to iterate the next relevant entry in the database of molecule descriptions. When the relevant entries in the database of molecule descriptions are completely processed, the index construction process 500 continues to a 'save indexing system' procedure 515 that can optimize and/or compress the 'locator data' and perform any bookkeeping procedures to generate an index that can be used by the indexing system. The index construction process 500 completes through an 'end' terminal 517.

In some embodiments (for example, but without limitation, indexing systems into protein databases), the list header for an IJ pair can associate a b-ion list and a y-ion list. In some of these embodiments, entries in the b-ion list specify 'locator data' that identifies the peptide description matching the associated index peak pair (IJ) as successive b-ions. Entries in the y-ion list specify 'locator data' that identifies the peptide description matching the associated index peak pair (IJ) as successive y-ions. Similar techniques can be used to improve performance of the indexing system for other databases of molecular descriptions.

Figure 6:
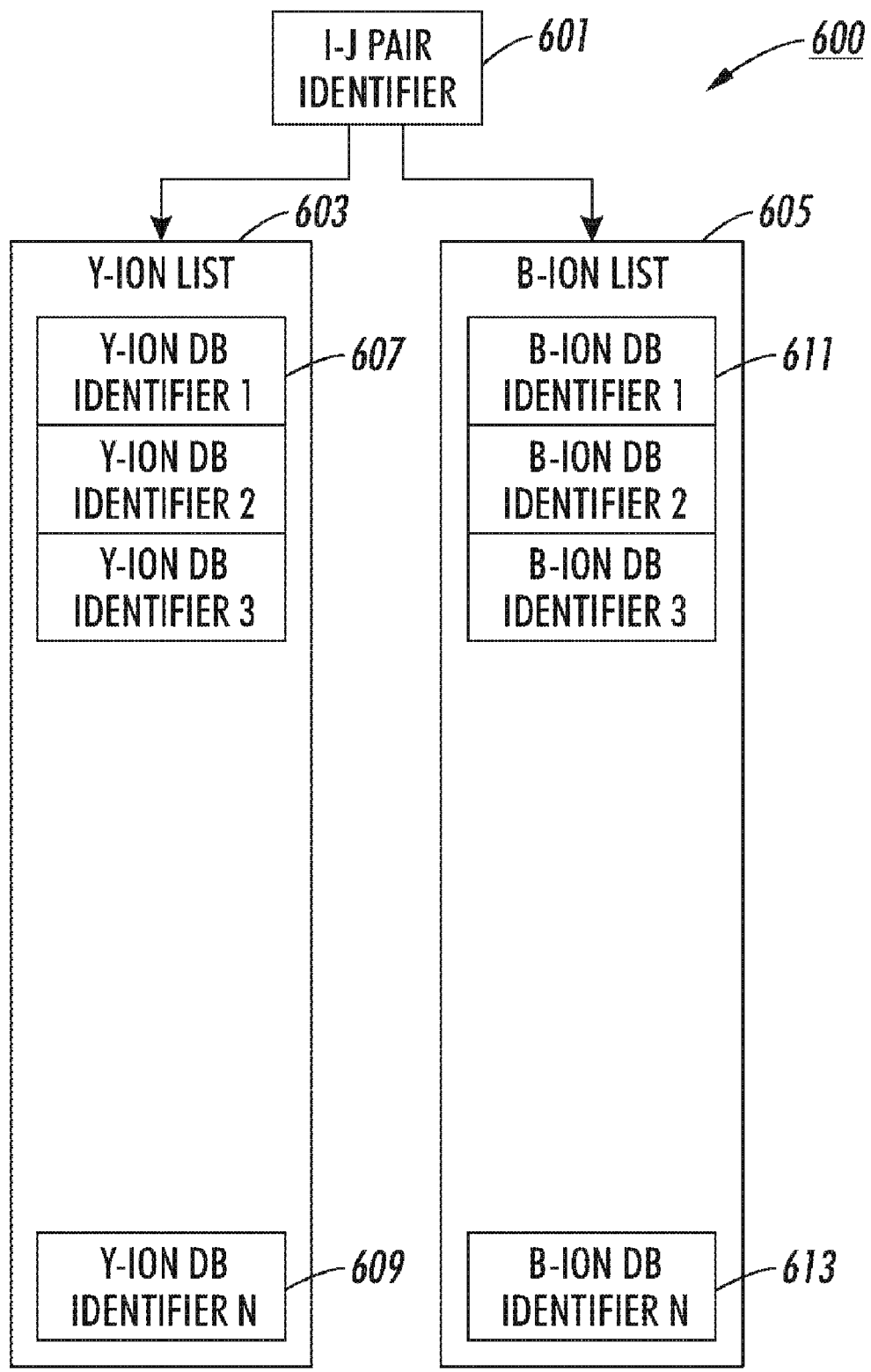
FIG. 6 illustrates a indexing system into a database of molecule descriptions.

FIG. 6 illustrates an indexing system 600 that includes a query identifier 601 that references a y-ion list 603 and a b-ion list 605. These lists contain entries such as a first y-ion database (DB) identifier 607 through an nth y-ion DB identifier 609 that contain information used to locate a particular string of amino acids in the database of molecule descriptions that match the associated index peak pair (IJ) and is a y-ion. A first b-ion DB identifier 611 through an $n^{th}$ b-ion DB identifier 613 provide similar information but for b-ions. Similar lists can be used in indexing systems directed to databases of other types of macromolecules. The indexing system 600 can be stored in the memory 205, on the network 209, on the storage system 215, on the tangible computer-usable data carrier 219, or in dedicated hardware for performing the indexing function into the database of molecule descriptions 117. The indexing system 600 can be provided to a user with the tangible computer-usable data carrier 219 or via the network 209. The indexing system 600 provides efficient access to a database of molecule descriptions by allowing queries to be used to quickly access the database of molecule descriptions without the size of the database of molecule descriptions One skilled in the art will understand that these lists can include arrays, linked lists, arrays, associate arrays, hashed indexes, structures or any other direct or indirectly referenced storage mechanism.

To summarize, parent ion-mass is a very weak filter for candidate peptides. For ion-trap instruments, parent ion-mass is typically known only within a range of about 3 Daltons. (For more accurate instruments, due to the clustering of peptide masses, it may still be known only to the closest integer.). With a 3-Dalton range, each residue in a peptide has about a 3% chance of completing a peptide that fits the parent-ion mass, because residues average about 100 Daltons. Thus accessing a 1-billion-residue database by parent-ion mass will return 30 million candidates, a rather unwieldy quantity, severely limiting the complexity of the scorer.

A 3-letter 'sequence tag' is a much stronger filter than the parent ion-mass filter. Each residue in a peptide has about a 0.013% chance of completing a given 3-letter tag (about 1 chance in 20 for each of the three letters, so 1/(20*20*20) chance overall). Thus sequence tagging will return 130,000 candidates.

A single query pair (IJ) is a medium-strong filter. Each residue R in a peptide has about a 0.05% chance of completing a given query pair (IJ) with b-ions (about 1 chance in 100 that the residues before R match I, and 1 chance in 20 that R matches J minus I). Thus R has about a 0.1% chance of matching the query pair (IJ) with either b-ions or y-ions. Thus a query pair (IJ) will return about 1 million candidates. The filtering of a query pair (IJ) is thus lower than that of a 3-letter tag, but a query pair (IJ) is much easier to compute than the 'sequence tag', which requires detection of 3 successive pairs, all of which must be simultaneously correct.

When the parent ion-mass and query pair (IJ) filters are combined, they become a very strong filter (3%*0.1%), returning only 30,000 candidates.

From the foregoing, it will be appreciated that the technology has (without limitation) the following advantages:

It increases performance of current parent-mass database search programs by a factor of 10×-1000×, without losing more than about 5% to 10% of the current identifications. (Notice, the 'sequence tag' approach also speeds up database search by such a factor, but will lose more candidates then the technology disclosed herein.)

It identifies many new candidates (especially of mutated or modified peptides) by enabling searches using a wider parent ion mass tolerance.

It allows the user to "tune" the number of "hits" to fit the circumstances. For example a user may generally require two matches from the query pairs (IJ), but for a "tryptic peptide" (one ending in or preceded by R or K) the user may require only a single match from the query pairs (IJ).

It can handle low-quality and mixture fragmentation spectra because it uses minimal de novo processing to determine the query peak (I) or the query pair (IJ).

It can be tuned to the quality of the fragmentation spectra because it is more robust to discrepancies than the parent ion-mass method (because a change to a single subunit of a macromolecule changes only about half of the peaks in the spectrum (the peaks coming "after" the change)).

It is able to identify candidates in spectra from "wide-window" tandem mass spectrometry (in which the parent ion-mass has a wide range of possible values).

It allows the use of lower-quality databases (such as the 2× and 4× genome data currently being produced) and more difficult spectra (such as spectra resulting from the mixtures that arise in wide-window MS/MS).

As used herein, a procedure is a self-consistent sequence of steps that can be performed by logic implemented by a programmed computer, specialized electronics or other circuitry or a combination thereof that lead to a desired result. These steps can be defined by one or more computer instructions. These steps can be performed by a computer executing the instructions that define the steps. Further, these steps can be performed by circuitry designed to perform the steps. Thus, the term "procedure" can refer (for example, but without limitation) to a sequence of instructions, a sequence of instructions organized within a programmed-procedure or programmed-function, a sequence of instructions organized within programmed-processes executing in one or more computers, or a sequence of steps performed by electronic or other circuitry, or any logic.

One skilled in the art will understand that the network transmits information (such as informational data as well as data that defines a computer program). The information can also be embodied within a carrier-wave. The term "carrier-wave" includes electromagnetic signals, visible or invisible light pulses, signals on a data bus, or signals transmitted over any wire, wireless, or optical fiber technology that allows information to be transmitted over a network. Programs and data are commonly read from both tangible physical media (such as a compact, floppy, or magnetic disk) and from a network. Thus, the network, like a tangible physical media, is a computer-usable data carrier.

Although the present technology has been described in terms of the presently preferred embodiments, one skilled in the art will understand that various modifications and alterations may be made without departing from the scope of the technology. Accordingly, the scope of the technology is not to be limited to the particular technology embodiments discussed herein.

What is claimed follows:

1. A computer controlled method comprising:
   selecting an existing representation of a macromolecule that includes a plurality of molecular subunits;
   determining a reference mass corresponding to a subset of the molecular subunits;
   determining an adjacent ion mass, wherein the adjacent ion mass is the sum of the reference mass and mass of an additional molecular subunit; and
   indexing, at a computer, a number of database records based at least on the reference mass and the adjacent ion mass, wherein a respective database record includes a representation of a macromolecule, and wherein the database records are directly indexed by the reference mass and the adjacent ion mass.

2. The computer controlled method of claim 1, further comprising creating a database of molecule descriptions comprising said macromolecule structure, said reference mass and said adjacent ion mass.

3. The computer controlled method of claim 1, wherein said macromolecule structure represents one or more molecules selected from a group consisting of a polymer, a lipid, a protein, a peptide and a glycan.

4. The computer controlled method of claim 1, further comprising providing a tangible computer-usable data carrier that includes said indexing system.

5. An apparatus having a processing unit (CPU) and a memory coupled to said CPU comprising:
   a selection logic configured to select an existing representation of a macromolecule that includes a plurality of molecular subunits;
   a determination logic configured to determine a reference mass corresponding to a subset of the molecular subunits and an adjacent ion mass, wherein the adjacent ion mass is the sum of the reference mass and mass of an additional molecular subunit; and
   an indexing mechanism configured to index a number of database records based at least on the reference mass and the adjacent ion mass, wherein a respective database record includes a representation of a macromolecule, and wherein the database records are directly indexed by the reference mass and the adjacent ion mass.

6. The apparatus of claim 5, further comprising a database output logic configured to create a database of molecule descriptions comprising said macromolecule structure, said reference mass and said adjacent ion mass.

7. The apparatus of claim 5, wherein said macromolecule structure represents one or more molecules selected from a group consisting of a polymer, a lipid, a protein, a peptide and a glycan.

8. A computer program product comprising:
   a tangible computer-usable data carrier providing instructions that, when executed by a computer, cause said computer to perform a method comprising:
      selecting an existing representation of a macromolecule that includes a plurality of molecular subunits;
      determining a reference mass corresponding to a subset of the molecular subunits;
      determining an adjacent ion mass, wherein the adjacent ion mass is the sum of the reference mass and mass of an additional molecular subunit; and
      indexing a number of database records based at least on the reference mass and the adjacent ion mass, wherein a respective database record includes a representation of a macromolecule, and
   wherein
      the database records are directly indexed by the reference mass and the adjacent ion mass.

9. The computer program product of claim 8, further comprising creating a database of molecule descriptions comprising said macromolecule structure, said reference mass and said adjacent ion mass.

10. The computer program product of claim 8, wherein said macromolecule structure represents one or more molecules selected from a group consisting of a polymer, a lipid, a protein, a peptide and a glycan.

11. The computer program product of claim 8, further comprising providing a computer-usable data carrier that includes said indexing system.

* * * * *